(12) United States Patent
Pope et al.

(10) Patent No.: US 6,321,595 B1
(45) Date of Patent: Nov. 27, 2001

(54) CHARACTERIZATION OF ORGANIC CONTAMINANTS AND ASSESSMENT OF REMEDIATION PERFORMANCE IN SUBSURFACE FORMATIONS

(75) Inventors: Gary A. Pope; Richard E. Jackson, both of Austin, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/312,755

(22) Filed: May 17, 1999

Related U.S. Application Data

(62) Division of application No. 08/377,742, filed on Jan. 23, 1995, now abandoned.

(51) Int. Cl.$^7$ .......................... E21B 47/10; E21B 49/08; G01N 33/26
(52) U.S. Cl. ................... 73/152.39; 73/152.41; 73/152.42; 166/252.2; 166/252.5; 166/310; 436/27; 436/29
(58) Field of Search .......................... 73/152.39, 152.41, 73/152.42; 436/27, 29; 166/252.2, 252.5, 310

(56) References Cited

U.S. PATENT DOCUMENTS

| | | |
|---|---|---|
| 3,590,923 | 7/1971 | Cooke ................................. 166/252 |
| 3,623,842 | 11/1971 | Deans ..................................... 23/230 |
| 4,158,957 | 6/1979 | Deans et al. ............................. 73/19 |
| 4,168,746 | 9/1979 | Sheely .................................. 166/252 |
| 4,742,873 | 5/1988 | Craig, III ............................. 166/252 |
| 5,168,927 | 12/1992 | Stegemeier et al. ................. 166/252 |
| 5,256,572 | * 10/1993 | Tang et al. ............................. 436/27 |
| 5,286,385 | * 2/1994 | Jorgensen et al. .................... 210/610 |
| 5,319,966 | 6/1994 | Jackson et al. ........................ 73/153 |
| 5,487,834 | 1/1996 | Carman et al. ....................... 210/606 |
| 5,615,974 | 4/1997 | Land et al. ............................ 405/128 |
| 5,687,093 | 11/1997 | Long et al. ............................ 364/512 |

OTHER PUBLICATIONS

Dwarakanath, V., et al. "New approach for estimating alcohol partition coefficients between nonaqueous phase liquids and water" Environ. Sci. Technol. vol. 32, No. 11, pp. 1662–1666, 1998.*

Lee, C. et al. "NAPL compositional changes influence partitioning coefficients" Environ. Sci. Technol. vol. 32, No. 22, pp. 3574–3578, 1998.*

Co–pending U.S. application SN 08/938,236 filed Sep. 26, 1997 (UTSB:644), now US 5,905,036.

Co–pending U.S. application SN 08/938,290 filed Sep. 26, 1997 (UTSB:645), now US 6,003,365.

Allison et al., "Analysis of Field Tracers for Reservoir Description," *Journal of Petroleum Science and Engineering*, 5:173–186, 1991.

Barua et al., "Improved Estimation Algorithms for Automated Type–Curve Analysis of Well Test," *SPE Formation Evaluation*, 186–196, Mar., 1988.

Bowman and Gibbens, "Difluorobenzoates a Nonreactive Tracers in Soil and Ground Water," *Ground Water*, 30(1):8–14, Jan.–Feb., 1992.

Brown and Pope, "Simulation of Surfactant–Enhanced Aquifer Remediation," *Water Resources Research*, 30(11):2959–2977, Nov., 1994.

Carrera and Neuman, "Estimation of Aquifer Parameters Under Transient and Steady State Conditions: 1. Maximum Likelihood Method Incorporating Prior Information," *Water Resourc. Res.*, pp. 199–210, accepted Oct. 25, 1985, published 1986.

Chavent et al., "History Matching by Use of Optimal Theory," *Society of Petroleum Engineers Journal*, pp. 74–86, Feb., 1975.

Cooley, "A Method of Estimating Parameters and Assessing Reliability for Models of Steady State Groundwater Flow. 1. Theory and Numerical Properties," *Water Resources Research*, 13(2):318–324, Apr., 1977.

Deans, H.A., "Using Chemical Tracers to Measure Fractional Flow and Saturation In Situ," *SPE of AIME*, Society of Petroleum Engineers, Symposium on Improved Oil Recovery, paper 7076, 1978.

Delshad et al., "a Compositional Simulator for Modeling Surfactant Enhanced Aquifer Remediation," submitted to *Journal of Contaminant Hydrology* Jan., 1995.

Jahns, "A Rapid Method for Obtaining a Two–Dimensional Reservoir Description From Well Pressure Response Data," *SPE Journal*, 6:315–327, Dec., 1966.

Jin et al., Subsurface Napl Contamination: Partitioning Tracer Test for Detection, Estimation and Remediation Performance Assessment, *Toxic Substances and the Hydrologic Sciences American Institute of Hydrology*, 131–159, 1994.

Johnson and Pankow, "Dissolution of Dense Chlorinated Solvents into Groundwater. 2. Source Functions for Pools of Solvent," *Environ. Sci. Technol.*, 26:896–901, 1992.

(List continued on next page.)

*Primary Examiner*—Gary Geist
*Assistant Examiner*—Leigh C. Maier
(74) *Attorney, Agent, or Firm*—Baker Botts L.L.P.

(57) ABSTRACT

Characterization of organic contaminants in subsurface formation is performed by methods for detecting the presence of nonaqueous phase liquid in a subsurface formation, and for determining the composition and for determining the volume of nonaqueous phase liquids. Generally the methods comprise introducing one or more partitioning tracers and one or more non-partitioning tracers at one or more injection points located in the subsurface formation and measuring separation between the one or more partitioning tracers and the one or more non-partitioning tracers from one or more sampling points located in the subsurface formation to determine presence, composition and/or volume of nonaqueous phase liquid in the subsurface formation. In addition, the methods can be used to assess the performance of an attempted remediation.

68 Claims, 7 Drawing Sheets

OTHER PUBLICATIONS

Kool and Parker, "Analysis of the Inverse Problem for Transient Unsaturated Flow," *Water Resources Research*, 24:817–830, Jun., 1988.

Lichtenberger, "Field Applications of Interwell Tracers for Reservoir Characterization of Enhanced Oil Recovery Pilot Areas," *SPE*, 209–221, 1991.

Mayer and Miller, "The Influence of Porous Medium Characteristics and Measurement Scale on Pore–Scale Distributions of Residual Nonaqueous–Phase Liquids," *Journal of Contaminant Hydrology*, 11:189–213, 1992.

Mercer and Cohen, "A Review of Immiscible Fluids in the Subsurface: Properties, Models, Characterization and Remediation," *Journal of Contaminant Hydrology*, 6:107–163, 1990.

Mishra and Parker, "Parameter Estimation for Coupled Unsaturated Flow and Transport," *Water Resources Research*, 25(3):385–396, Mar. 1989.

Newman and Yakowitz, "A Statistical Approach to the Inverse Problem of Aquifer Hydrology," *Water Resources Research*, 15(4):845–860, Aug., 1979.

Pickens et al., "Simulation of DNAPL Migration and Surfactant Enhanced Aquifer Remediation," Presentation for Hazmat Southwest Conference, Sep., 1993.

Petrobrás and Horne, "Automated Well Test Analysis Using Robust (LAV) Nonlinear Parameter Estimation," *SPE*, 191–206, 1991.

Russo et al., "Analyses of Infiltration Events in Relation to Determining Soil Hydraulic Properties by Inverse Problem Methodology," *Water Resources Research*, 27(6):1361–1373, Jun., 1991.

Senum et al., "Petroleum Reservoir Characterization by Perfluorocarbon Tracers," SPE/DOE paper No. 24137, 1992.

Shah et al., "Error Analysis in History Matching: The Optimum Level of Parameterization," *Society of Petroleum Engineers Journal*, 219–228, Jun., 1978.

Sheely, "Description of Field Tests to Determine Residual Oil Saturation by Single–Well Tracer Method," *Journal of Petroleum Technology*, 194–202, Feb., 1978.

Sheely and Baldwin, "Single–Well Tracer Tests for Evaluating Chemical Enhanced Oil Recovery Processes," *Journal of Petroleum Technology*, 1887–1896, Aug., 1982.

Sykes et al., "Numerical Simulation of Flow and Contaminant Migration at an Extensively Monitored Landfill," *Water Resources Research*, 18(6):1687–1704, Dec., 1982.

Smith et al., "Analysis of Unsteady–State Displacements Using a Capacitance–Dispersion Model," In Situ, 12(1&2):41–78, 1988.

Strecker and Chu, "Parameter Identification of a Ground-–Water Contaminant Transport Model," *Ground Water*, 24(1):56–62, Jan., 1986.

Sudicky, "A Natural Gradient Experiment of Solute Transport in a Sand Aquifer: Spatial Variability of Hydraulic Conductivity and Its Role in the Dispersion Process," *Water Resources Research*, 22(13):2069–2082, Dec., 1986.

Sun and Yeh, "Coupled Inverse Problems in Groundwater Modeling, 1. Sensitivity Analysis and Parameter Identification," *Water Resources Research*, 26(10):2507–2525, Oct., 1990.

Sun and Yeh, "Coupled Inverse Problems in Groundwater Modeling, 2. Identifiability and Experimental Design," *Water Resources Research*, 26(10):2527–2540, Oct., 1990.

Tang, "Interwell Tracer Tests to Determine Residual Oil Saturation to Waterflood at Judy Creek BHL "A" Pool," *The Journal of Canadian Petroleum Technology*, 31(8):61–71, Oct., 1992.

Tang and Harker, "Interwell Tracer Test to Determine Residual Oil Saturation in a Gas–Saturated Reservoir. Part I: Theory and Design," *The Journal of Canadian Petroleum Technology*, 30(3):76–85, May–Jun., 1991.

Tang and Harker, "Interwell Tracer Test to Determine Residual Oil Saturation in a Gas–Saturated Reservoir. Part II: Field Applications," *The Journal of Canadian Petroleum Technology*, 30(4):34–42, Jul.–Aug., 1991.

Tomich et al., "Single–Well Tracer Method To Measure Residual Oil Saturation," *Journal of Petroleum Technology*, 211–218, Feb., 1973.

Umari, A., "Identification of awuifer dispersivities in two–dimensional transient groundwater contaminant transport: and optimization approach," *Water Resources Res.*, 15(4):815–831, Aug. 1979.

Wagner and Gorelick, "Optimal groundwater quality management under parameter uncertainty," *Water Resources Res.*, 23(7):1162–1174, Jul. 1987.

Whitley et al., "Nonaqueous phase liquid characterization using partitioning gas tracers in the Vadose Zone: an experimental investigation," submitted for publication to *Environmental Science and Tech.*, Nov. 10, 1994.

Yeh, W., "Review of parameter identification procedures in groundwater hydrology: the inverse problem," *Water Resources Res.*, 22(2):95–108, Feb. 1986.

Yeh, W., "Aquifer parameter identification with optimum dimension in parameterization," *Water Resources Res.*, 17(3):664–672, Jun. 1981.

\* cited by examiner

Comparison of Experimental and Simulated Tracer Responses

CHARACTERIZATION OF ORGANIC CONTAMINANTS AND ASSESSMENT OF REMEDIATION PERFORMANCE IN SUBSURFACE FORMATIONS

This is a divisional of co-pending application Ser. No. 08/377,742, filed Jan. 23, 1995, now abandoned.

FIELD OF INVENTION

This invention concerns methods of detecting the presence of contaminants located in subsurface formations, methods of determining the composition and/or volume of the contaminants and methods of assessing the performance of remediation designed to treat or remove contaminants from subsurface formations.

BACKGROUND OF INVENTION

In the 1980's, it became apparent that many hazardous waste sites had received organic liquids, such as petroleum hydrocarbons, chlorinated solvents, creosote solutions and coal tars which had subsequently migrated into the subsurface beneath these sites. Once in the subsurface, these liquids dissolved and caused the contamination of groundwater supplies and then proved resistant to their quantitative removal by the remedial approaches available. These liquids are known to environmental scientists and engineers as non-aqueous phase liquids, or "NAPLs". NAPLs such as petroleum hydrocarbons, which are lighter than water, are identified as "lLNAPLs", while those denser than water such as chlorinated solvents are known as "DNAPLs".

NAPLs are generally of sufficiently low aqueous solubility and volatility that their limited dissolution into ground waters or volatilization into gases has resulted in predictions of their residence in the subsurface for tens, hundreds or perhaps thousands of years. However, their toxicity is often such that their solubilities are many times the permitted maximum contaminant levels allowed by the U.S. Environmental Protection Agency in drinking water. For example, the most common NAPL contaminant found in ground waters beneath hazardous waste sites, the metal degreasing solvent trichloroethene, has an aqueous solubility of 1385 milligrams/liter but a maximum contaminant level of 5 micrograms/liter.

Partly because of their ubiquitous use in industry and commerce, low maximum contaminant levels and mobility in the subsurface in dissolved and gaseous states, NAPLs and NAPL constituents, such as benzene derived from gasoline, have come to occupy a central place in the technical and regulatory processes associated with the characterization and remediation of hazardous waste sites. In addition, NAPLs have become the focus of this concern because of the extreme difficulty in detecting their presence. In the context of this discussion, "detection" means the act of inferring the amount, location and/or composition of the NAPL. In recent years, a number of knowledgeable observers have commented on the cost and impracticality of detecting DNAPLs using conventional site-characterization techniques. See, for example, Huling and Weaver, *DNAPL site evaluation, Project Summary*, EPA/600/SR-93/022, U.S. Environmental Protection Agency, R.S. Kerr Environmental Research Laboratory, Ada, Okla., 74820 (1993); Cohen and Mercer, *Dense nonacueous phase liquids. Ground Water Issue*, EPA/540/4-91-002, U.S. Environmental Protection Agency, R.S. Kerr Environmental Research Laboratory, Ada, Okla., 74820 (1989); MacKay and Cherry, "Groundwater Contamination:Pump-and-treat Remediation," *Environmental Science and Technology*, 23(6):630–636 (1993).

However, despite the expenditure of billions of dollars annually by the U.S. Government through the Environmental Protection Agency (for instance, in the implementation of Superfund), the U.S. Department of Energy (implementing the Environmental Restoration Program), the U.S. Department of Defense (implementing the Installation Restoration Program), as well as private corporations, the U.S. Environmental Protection Agency reported in April, 1993 (Cohen and Mercer, 1993) that "relatively little effort has been expended on developing new site-characterization tools or methods for DNAPL sites." This situation has resulted in substantive problems for DNAPL site characterization, in particular because of the tendency of DNAPLs, due to their density and viscosity, to migrate both vertically and laterally from their point of entry into the subsurface to considerable depth. Consequently, DNAPLs are "largely undetected and yet are likely to be a significant limiting factor in site remediation" (Huling and Weaver, 1991).

It follows from the sparing solubility and volatility of NAPLs that, generally, the vast majority of the mass of an organic liquid released to the subsurface may remain in the NAPL form. Relatively minuscule concentrations will be present in the dissolved and vapor states, but it is these less important phases that are generally monitored for compliance with regulations concerning the performance of the remedial operations at a site (see, Environmental Protection Agency, "General methods for remedial operations performance evaluations-" EPAl600/R092/002, R.S. Kerr Environmental Research Laboratory, Ada, Okla. 74820 (1992)).

SUMMARY OF THE INVENTION

It is now contemplated that one or more problems exist in the area of NAPL remediation, namely the inability to directly measure NAPL location, volume and composition and thereby quantitatively assess the performance of remedial technologies. Thus, the absence of reliable tools for detecting NAPLS, particularly DNAPLs, prevents successful remediation or perhaps even containment at hazardous waste sites because effective methods of remediation or containment or both cannot be focused on the source of contamination when the location, amount and perhaps composition of the source are unknown. Furthermore, without direct quantitative measures of NAPL volume and composition, the performance of remediation technologies cannot be assessed.

The present invention provides a solution to one or more of the needs and disadvantages discussed above. This invention provides a significant development in the context of contaminant remediation by providing a process to, in the first instance, detect whether a NAPL is present. In addition, this invention further supplies a method to assess the performance of an attempted remediation by measuring the volume of NAPL in the subsurface both before and after the attempted remediation. Still further, this invention provides a process for ascertaining the composition of the NAPL located in the subsurface prior to remediation, thereby enabling the design of the remediation which is specifically directed to removal of the thus identified constituents of the NAPL. The several aspects of this invention will now be described.

This invention, in one respect, is a method for detecting the presence of nonaqueous phase liquid in a subsurface formation, comprising:

(A) introducing one or more partitioning tracers and one or more non-partitioning tracers at one or more introduction points located in the subsurface formation;

(B) measuring separation between the one or more partitioning tracers and the one or more non-partitioning tracers from one or more sampling points to determine whether nonaqueous phase liquid is present in the subsurface formation.

This invention, in a second respect, is a method for detecting the presence of dense nonaqueous phase liquid located in a subsurface formation, comprising:

(A) introducing one or more partitioning tracers and one or more non-partitioning tracers into one or more introduction points located in the subsurface formation;

(B) measuring separation between the one or more partitioning tracers and the one or more non-partitioning tracers from one or more sampling points to determine whether dense nonaqueous phase liquid is present.

This invention, in a third respect, is a method for determining a three dimensional distribution of nonaqueous phase liquid located in a subsurface formation, comprising:

(A) introducing one or more non-partitioning tracers into one or more injection points located in the subsurface formation;

(B) withdrawing the one or more non-partitioning tracers and one or more partitioning tracer from one or more sampling points located in the subsurface formation; wherein the introducing occurs at two or more depths or the withdrawing occurs at two or more depths or wherein both the withdrawing and the introducing occur at two or more depths;

(C) measuring separation between the one or more non-partitioning tracers and the one or more partitioning tracers from the one or more sampling points to determine the three dimensional distribution of nonaqueous phase liquid in the subsurface formation.

This invention, in a fourth respect, is a method for determining a composition of nonaqueous phase liquid located in a subsurface formation, comprising:

(A) introducing one or more non-partitioning tracers and twc or more partitioning tracers into one or more introduction points located in the subsurface formation;

(B) measuring separation between the one or more non-partitioning tracers and the two or more partitioning tracers from one or more sampling points;

(C) comparing the measured separation with reference separation of the one or more non-partitioning tracers and the two or more partitioning tracers when contacted with known nonaqueous phase liquids to determine the identity of the nonaqueous phase liquids in the subsurface formation.

This invention, in a fifth respect, is a method for determining a volume of dense nonaqueous phase liquid located in a subsurface formation, comprising:

(A) introducing one or more non-partitioning tracers and one or more partitioning tracers into one or more introduction points located in the subsurface formation;

(B) measuring separation between the one or more non-partitioning tracers and the two or more partitioning tracers from one or more sampling points to determine the volume of dense nonaqueous phase liquids in the subsurface formation.

In a sixth respect, this invention is a method for assessing the performance of attempted remediation of dense nonaqueous phase liquid located in a subsurface formation, comprising:

(A) introducing one or more non-partitioning tracers and one or more partitioning tracers into one or more injection points located in the subsurface formation;

(B) measuring separation between the one or more non-partitioning tracers and the two or more partitioning tracers from one or more sampling points to determine the volume of dense nonaqueous phase liquids in the subsurface formation;

(C) performing an attempted remediation to treat or remove nonaqueous phase liquid in the subsurface formation;

(D) repeating steps (A) and (B) to assess performance of the attempted remediation.

DETAILED DESCRIPTION OF THE INVENTION

Figure 1:
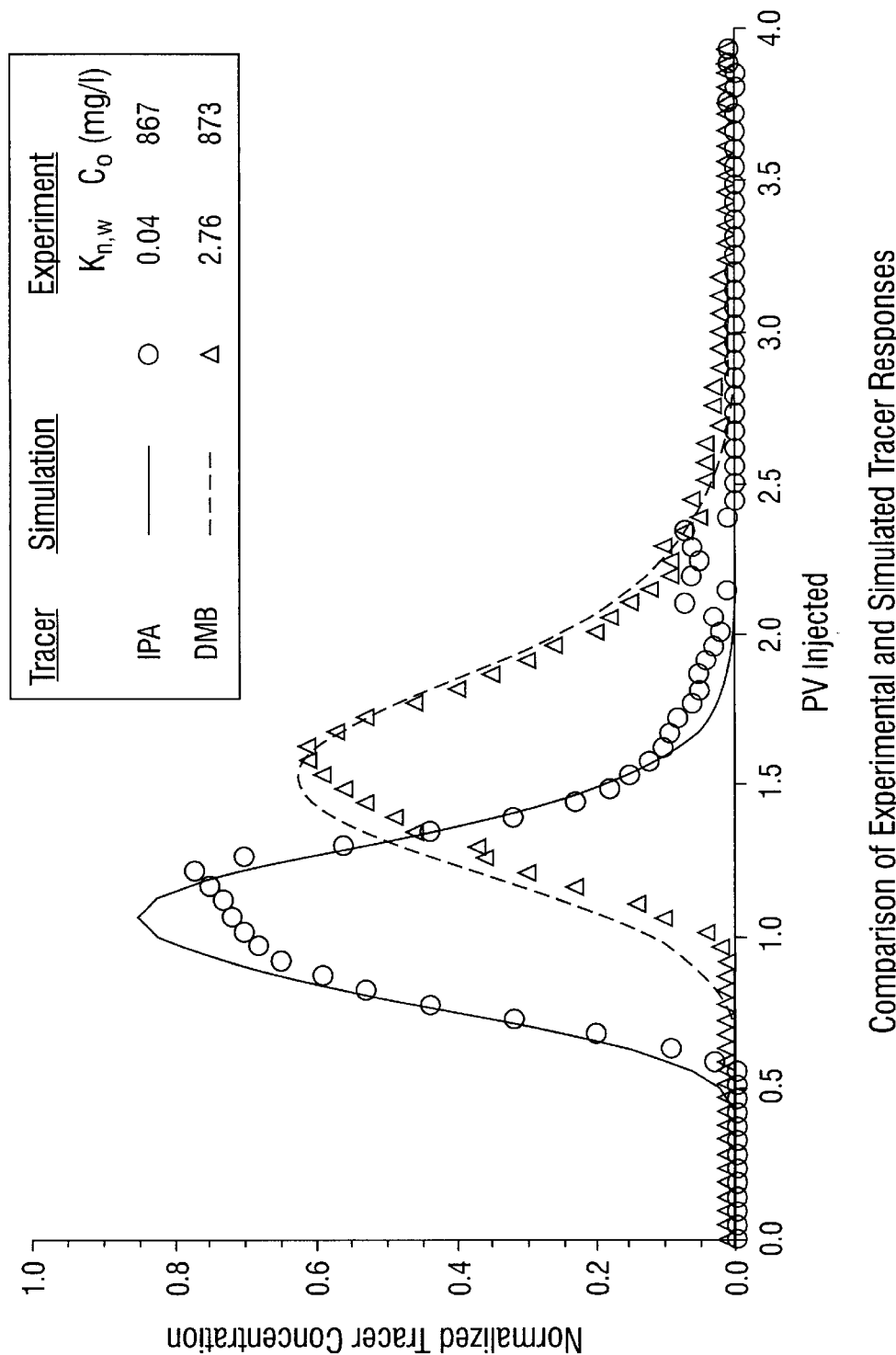
FIG. 1 shows a chromatogram from Example 1 of the normalized concentration of tracers plotted against pore volumes.

The amount of tracer used in the practice of this invention will vary depending on NAPL volume, pore volume of the subsurface to be investigated and detection limits of the detection equipment employed. Generally, however, the tracers are employed in an amount such that the tracer concentration at sampling points will exceed a minimum detection levels for the analytical a instrument suitable for the conditions of interest.

Generally, in the first step of the practice of the invention, partitioning and nonpartitioning tracers are introduced into a subsurface formation. The partitioning tracers are characterized as having the property of partitioning into the: NAPL to a greater extent than the nonpartitioning tracer such that the partitioning tracer travels in the subsurface formation at a slower rate than the nonpartitioning tracer. For example, depending on the NAPL in the subsurface formation, a six-carbon alcohol (e.g., dimethylbutanol) might partition into the NAPL more than a three-carbon alcohol (e.g., isopropanol) such that the lighter alcohol travels through the subsurface formation more rapidly than the heavier alcohol. This concept is similar to the elution of disparate substances through a chromatography bed to separate the disparate substances. The partition coefficient of a given tracer provides an indication of the relative partitioning to be expected in the practice of this invention. Appropriate tracers can be selected from partitioning information to select at least one nonpartitioning tracer and one or more partitioning tracers (relative to the partition coefficient of the nonpartitioning tracer).

Generally, it is contemplated that the tracers will be introduced into the subsurface formation via a carrier fluid. In one embodiment of this invention, the carrier fluid is a liquid such as water. In another embodiment of this invention, the carrier fluid is gaseous at ambient temperatures, such as air.

A wide variety of tracers can be used in the practice of this invention and virtually any compound can be used as a tracer with the proviso that the tracer has a different composition from the NAPL. Representative classes of useful tracers include alcohols, perfluorocarbons, perfluorosulfur compounds, esters, amines, amides, hydrocarbons, sulfates, aldehydes, ketones, as well as salts of bromide and iodide. Representative examples of useful alcohols include $C_1$–$C_{20}$ alcohols and polyhydric alcohols. Representative examples of useful perfluorocarbons include carbon tetrafluoride ($CF_4$), octafluorocyclobutane ($C_4F_8$), octafluorocyclopentene ($C_5F_8$), dodecafluorodimethylcyclobutane ($C_6F_{12}$), perfluoromethylcyclohexane ($C_7F_{14}$) and perfluoro-1,3-dimethylcyclohexane ($C_8F_{16}$). When a liquid carrier fluid is employed, preferred tracers are alcohols. When the carrier fluid is gaseous, preferred tracers are perfluorocarbons.

The amounts of tracers will vary widely depending on a variety of factors well known to those skilled in the art. Such factors include but are not limited to the type of tracers employed, the pore volume of the subsurface formation (pore volume being defined as the volume of pore space encountered by the tracers between the introduction points and sampling points), the NAPL saturation in the subsurface formation (defined as the volume fraction of NAPL per unit pore space in the subsurface formation), the distance between introduction points and extraction (or "sampling") points, the geology of the subsurface formation and the partition coefficients of the tracers.

The tracers used here can be reactive tracers including chemically reactive tracers and biologically reactive tracers.

Chemically reactive tracers typically comprise substances such as esters which hydrolyze during the practice of this invention to form an alcohol and a carboxylic acid with the resulting alcohol and unreacted ester functioning as the tracers. For example, ethyl acetate and propyl formate hydrolyze to form, respectively, ethanol and propanol. Use of chemically reactive tracers is advantageous in circumstances where the introduction point and the sampling point are at the same location. The use of chemically reactive tracers enhances the signal produced in the measurement equipments. It should be appreciated a soak time may be needed to enable the tracers to react, such as to hydrolyze. Use of chemically reactive tracers is not, however, limited to such applications. Thus, owing to the relatively short times that tracers spend in the soil traveling along streamlines between wells, reactive tracers could also be used in the practice of any other aspects of this invention. Representative examples of useful esters include ethyl acetate, methyl acetate, isopropyl acetate, ethyl acetoacetate, ethyl acrolate, ethyl methacrolate, ethyl butylate, ethyl benzoate, propyl formate, ethyl formate, dimethyl maleate, dimethyl fomarate, dimethyl phthalate, dimethyl glutarate, dimethyl succinate, methyl salicylate, methyl methacrylate, methyl acrylate, isobutyl methacrylate, isobutyl acrylate, ethylene glycol monomethyl ether acetate, ethylene glycol monethyl ether acetate, ethylene glycol monobutyl ether acetate, ethyl oxalate, ethyl methacrylate, ethyl butylate and ethyl acrylate.

Biologically reactive tracers are substances which respond to microbiologically induced reactions indicative of the presence or absence of NAPL. For instance, such biologically reactive tracers may be capable of being used as a fuel or nutrient for given microorganisms. The use of biologically reactive tracers is envisioned in circumstances where the NAPL present in the subsurface environment is at a level prior to remediation sufficient to suppress the growth of microorganisms. When the given NAPL is removed sufficiently, the microorganisms may repopulate the subsurface or increase in population. In such cases, a biologically reactive tracer can be selected which the given microorganism feeds. It can thus be seen that the amount of biologically reactive tracer measured would diminish after remediation, thereby indicating a decrease in NAPL in the subsurface formation. For example, sulfates in a sulfate-reducing environment could be induced to reduce to sulfide by action of sulfate-reducing bacteria, the activity formerly being suppressed by presence of NAPL prior to remediation.

In another embodiment of the present invention, the tracers can be introduced into the subsurface formation together with a thickening agent. Thickening agents are advantageously employed in situations such as when the NAPL is geologically trapped in the soil, for example, in a zone of the permeable soil, whereby the NAPL is more difficult to contact efficiently with tracers. In such cases, it may be advantageous to include thickening agents with the tracers to provide a more viscous fluid which will slow the water preferentially where no NAPL exists and thereby help force the tracers into the NAPL zone. Food grade water-soluble polymers are readily available and useful for this purpose. It is thus apparent that in these applications the thickening agents serve to exert hydraulic control of the tracers introduced in the subsurface formation. Additionally, use of thickened tracer fluids may be advantageous in fractured formations. In such cases, the tendency of the water to flow preferentially through the fractures rather than the rock matrix that may contain the largest fraction of NAPL. Polymers of variable size may be used to advantage. Such large molecules may exhibit size exclusion effects as in gel permeation chromatography and others known to those of skill in the art. Such effects may aid both in placement of the tracers in the fractured formation and in the interpolation of the chromatographic signals of the tracers. Useful thickening agents vary widely but generally include water soluble polymeric substances having a molecular weight in the range from about one to about 20 million. Representative classes of useful thickening agents include polysaccharides, polyglycols and cellulose materials. Representative examples of such thickening agents t include xantham gum and carboxy methyl cellulose. The representative classes and examples of thickening agents is not intended to be an exhaustive list of such substances. The amount of thickening agents used will also vary depending on the amount of thickening desired and will also vary on the inherent viscosity of the thickening agent. Generally, an amount of thickening agent in the range from about 100 ppm to about 10,000 ppm can be employed.

The tracers used in the practice of this invention may be introduced into the subsurface formation by a variety of ways. For instance, the tracers can be introduced simply by digging a hole of desired depth, placing an amount of tracers in the hole and refilling the hole with the material previously removed. The tracers can also be introduced into the subsurface formation by a variety of well known methods employing well known means to achieve such methods. For example, tracers can be introduced by adding the tracers to a well such as an extraction or a monitoring well. Additionally, the tracers can be introduced via a piezometer, a stand pipe, a multilevel sampler, a drive point sampler or a cone-penetration sampling point. The tracers can be added all at once, intermittently or continuously over time. The rate of introduction of the tracers is generally not critical and will vary depending on the size and geology of the subsurface formation. Such rate can be determined by one of skill in the art. As discussed above, the amount of tracers employed will also vary depending on the size and geology of the subsurface formation, but generally will be an amount sufficient such that all the tracers introduced are in amounts which can be detected at the sampling points after the tracers travel a given distance through the subsurface formation. It is contemplated that the farther the distance between introduction point and sampling point, the larger the amount of tracers may be required.

In the practice of this invention, the tracers which have been introduced into the subsurface formation can be allowed to travel through the subsurface formation thereby allowing the natural gradients to carry the tracers. Preferably, the tracers are forced into the subsurface formation as by pumping, i.e. injecting, the tracers. Pumping may be accomplished using methods and equipment well known to those skilled in the art.

It is contemplated that the tracers can be introduced into the subsurface formation at one injection point or at multiple injection points. It should be appreciated that when multiple injection points are employed in the practice of this invention, the injection points may differ by depth only or differ from one another by lateral location or differ by combinations of different depths and lateral locations. Thus, in one embodiment of the present invention, the tracers can be introduced into the subsurface formation via a single well at a variety of depths. In another embodiment of the invention, the tracers can be introduced into the subsurface formation through multiple wells.

In the practice of this invention, it may be advantageous to minimize loss of tracer after injection into the subsurface formation by confinement of the surface. This technique would be particularly advantageous when a gaseous carrier fluid is employed. Confinement at the surface can be achieved as by covering the surface with a sheet of impervious material to seal the surface.

The tracers are detected and measured at a sampling point after a time sufficient to enable the tracers to travel through the subsurface formation. The sampling point can be at an injection point or can be a given distance from an injection point. Additionally, a sampling point can be in the subsurface formation or, alternatively, the tracers can be withdrawn above ground and measured thereafter. Preferably, an individual sampling point is a given distance from a given injection point. The measurement can occur at a sampling point below the surface such as when the measurement equipment is located in the subsurface formation or can occur above the subsurface after withdrawing the tracers from the subsurface formation at a sampling point. In principle it may be possible to affect surface detection of the subsurface tracers using electromagnetic or acoustic signals. Generally, however, detection is achieved by obtaining a sample of the tracers present (in a carrier fluid if a carrier fluid is used) and measuring any separation of tracers using conventional equipment such as liquid or gas chromatography instruments. It is also contemplated that multiple depth samplers can be useful in the practice of this invention, as when for example, a monitoring well is employed at the sampling location. Alternatively, measurement equipment equipped with a ion-selective electrode can be employed when the tracer is an ion such as iodide or bromide.

The chromatography equipment should provide the operator with a reading showing the separation of tracers. If NAPL is absent from the subsurface formation, no separation of tracers should occur, whereas if NAPL is present separation should occur.

The separation of tracers will enable the operator to determine the location, volume or composition of NAPL.

From the difference in production times of the tracers, i.e., the measured separation of tracers at the sampling point, the NAPL saturation in the subsurface formation can be determined. Using the method of moments, the volume of total NAPL in the subsurface formation is given by the formula:

$V_N = (\overline{V}_p - \overline{V}_n)/K$, where $\overline{V}_p$ and $\overline{V}_n$ are the first moments of the nonpartitioning and partitioning tracers in terms of cumulative volume of detected tracers at the sampling point, K is the partition coefficient of the partitioning tracer and $V_N$ is the volume of NAPL. This equation or others similar to it can be applied repeatedly to any number of tracers used in this way. For example, for tracers which are introduced as gases (see, for example, Table 1) the following equation can be employed: $V_N = q(\bar{t}_p - \bar{t}_n)/K_i$ wherein $K_i$ is the partition coefficient of tracer $K_i$ between the NAPL and air, $\bar{t}_p$ and $\bar{t}_n$ are the mean residence times of the partitioning and non-partitioning tracers obtained by integrating the two tracer response curves to estimate the first moments of these curves and q is the flow rate [$L^3/T$]. Additionally, the partition coefficient K of a gaseous tracer $K_i$ is the ratio of its concentration [$M/L^3$] in the NAPL phase to its concentration in the gaseous phase, according the formula:

$$K_i = C_{iN}/C_{ia}.$$

Using thermodynamic phase equilibria theory, partition coefficients for the various tracers and a particular NAPL may be estimated. The partition coefficient of tracer i between NAPL and air was given in an equation above and can be expanded to include mole fractions and density, or $K_i = (C_{iN}/C_{ia}) = (x_{iN}\rho_N/x_{ia}\rho_a) = (x_{iN}\overline{V}_a)/(x_{ia}\overline{V}_N)$, where $x_{ij}$ is the mole fraction of tracer i in phase j, $\overline{V}_a$ and $\overline{V}_N$ are the molar volumes of the air and NAPL phases [$L^3$/mole], respectively, and $\rho_j$ is the molar density of that phase. Since the gas phase can be assumed to be ideal at such low pressure, the partition coefficient can be estimated from the liquid phase activity coefficient $\gamma_i$ and the vapor pressure of each species i as follows: $K_i = (P\overline{V}_a)/(P_i^{vap}\overline{V}_N\gamma_i)$, where P is the total pressure [$F/L^2$], $P_i^{vap}$ is the vapor pressure of the tracer, and $\gamma_i$ is the activity coefficient for tracer i in the liquid phase. The molar volume of air at 23° C. is 24,300 cc/mole and the molar volume of TCE is 89.99 cc/mole. If the liquid phase were an ideal solution, then the Lewis-Randall rule would apply and the activity coefficient of the tracer in the NAPL would be one. These ideal $K_i$ values are listed in Table 2 for each tracer with trichloroethene. However, in practice, the liquid can be far from ideal. An activity coefficient model to estimate $\gamma_i$ can be used in such a case. For example, a regular solution theory model could be used when the species are not polar. However, such models should be well established for the precise conditions of interest to make predictions with a high level of confidence.

If the amounts of NAPL in different locations vertically and/or areally need to be determined, the combined chromatographic signal from the tracers needs to be inverted. In many contaminant detection problems, most of the soil will not be contaminated by NAPL, but only a small amount of NAPL where the source is located. This source often will have caused a plume of dissolved contaminant to form and migrate over large distances in ground water, but the source itself will often be small, of unknown location, and difficult to find by existing technology. A novel aspect of this invention is the use of multi-level tracer injection points and sampling points to solve the inverse problem required to determine the three-dimensional distribution of NAPL in the soil. When the location of NAPL is desired to be elucidated by the practice of this invention, one or more partitioning tracers and one or more nonpartitioning tracers may be introduced at multiple injection points or measured at multiple sampling points, or introduced at multiple injection points and measured at multiple sampling points.

Although most of the NAPL will typically be contained in the source, small amounts will often dissolve in the water and the amount so dissolved may also be of interest. A contaminated unsaturated zone generally consists of three fluid phases, namely, residual water, residual NAPL and air. Thus, knowing the residual water saturation may be valuable as well. In this case, one or more tracers that partition into the water from the carrier fluid could be used to estimate the residual water saturation at the same time that the same or other partitioning tracers are used to determine residual NAPL saturation.

The present invention can be employed to determine location, volume and/or composition of NAPL. It should be appreciated the composition of the NAPLs are oftentimes not known and may vary significantly within the subsurface formation since, in many cases, a wide variety of organic wastes was buried or disposed of over long periods of time in different points of the ground surface without sufficient records. Furthermore, the composition of the NAPL may have changed due to natural processes such as volatilization into the air, dissolution and so forth. Samples of air and water containing some of these components are not always a reliable indicator of the source composition and liquid samples are often not available. Tracer partition coefficients are a function of the NAPL composition, so this affects the design and interpretation of the practice of this invention in the field.

A novel aspect of this invention is the ability through practice of this invention to obtain useful results from partitioning tests even in situations where the NAPL composition is only known approximately. In such a case, laboratory experiments and/or thermodynamic theory can be used to estimate the K values of each tracer in each major organic species (component) of the NAPL. Provided at least as many partitioning tracers are used as there are major organic species (components of the NAPL), then the composition of the NAPL can be inferred as well as the amount of NAPL. This is a second type of inverse problem, known as "compositional analysis," since a solution to the set of equations describing the behavior of the tracers must be estimated from the multiple simultaneous tracer signals.

After the NAPL has been located and one or more of several remediation technologies has been applied to remove it from the soil, the quantity remaining in the remediated zone may be estimated to thereby provide a performance assessment of the attempted remediation. In another embodiment of this invention, the quantity of NAPL in the remediation zone can be determined concurrently with the remediation. Thus, the methods of this invention can be employed before, during and after attempted remediations To determine volume of NAPL present, one partitioning tracer and one nonpartitioning tracer need only be introduced into the subsurface formation.

In one embodiment of the present invention, the distribution of NAPL in the subsurface formation. In this regard, it is desirable to sampling the tracers at multiple sampling points and the use of modeling. In particular, appropriate injection and sampling points are determined, generally by injecting and/or sampling the tracers at different depths. In some cases, it may be desirable to repeat the tracer testing using different injection and/or sampling points both with respect to depth and surface location. Once three-dimensional data of this type has been obtained, a suitable inverse model can be used to calculate a three-dimensional distribution of NAPL. First, a suitable model of the fluid flow behavior of the tracers in the formation is obtained. This model will generally be either a streamline model with suitable features to model partitioning tracers or a finite difference or finite element numerical model that approximates the differential equations describing the three-dimensional fluid flow in the formation, but any suitable engineering approach could be used provided it included a description of the behavior of the partitioning tracers. Second, an algorithm for calculating parameters in this model is obtained. This model will generally be based upon a maximum likelihood method such as least squares regression that can be used to calculate an unknown parameter vector go as to fit the fluid flow model predicted values to measured data in a least squares sense. Such least squares regression algorithms are known to those of skill in the art, as described in Jin et al., "Subsurface NAPL Contamination: Partitioning Tracer Test for Detection, Estimation and Remediation Performance Assessment," *Toxic Substances and the Hydrolocf Sciences*, (American Institute of Hydrology, 1994), pages 131–159, incorporated herein by reference. The parameters in this instance will include the local NAPL saturations or equivalent measures of NAPL amount locally for discrete volumes of the contaminated formation under testing. Although other approaches to solving this inverse problem can be used, including even trial and error, these other methods will generally be less satisfactory. The forward fluid flow model can be used, and is preferably used, to calculate the appropriate injection and sampling points to design the tracer test for this purpose.

In addition to estimating the amount and location of NAPL within the contaminated formation from the partitioning tracer data, it may be desirable to estimate NAPL composition since many polluted subsurface waste sites contain mixtures of various contaminants. If the various chemical components of this waste mixture are not too dissimilar, a single organic liquid may be expected to occur within the pores of the contaminated soil or rock formation, but unless this liquid has been carefully sampled and analyzed, its precise composition (the set of mole fractions of each component in the mixture) will not be known. Estimates of its composition can sometimes be made from compositional measurements on contaminated water, air or soil that has been sampled and analyzed from locations hydraulically connected to the NAPL, but the reliability of these will vary depending on the nature of the NAPL and other poorly known factors, so additional information about the NAPL composition as inferred from the partitioning tracer test may be desired. This can be done provided a sufficient number of partitioning tracers are used since the partition coefficient of each tracer can be modeled as a function of NAPL composition and the tracer data inverted to infer composition. In particular, each tracer partition coefficient can be expressed as a function of the activity coefficient of each chemical component in the NAPL or alternatively some other equivalent thermodynamic model can be used to express the relationship between the partition coefficient and composition. Activity coefficients depend on the temperature, pressure and n-1 mole fractions, where n is the number of components in the NAPL. The temperature and pressure can be considered known and fixed for any given test. This means that n-1 partitioning tracer data sets are needed in principle to infer the n-1 mole fractions describing the unknown NAPL composition. In addition, one partitioning tracer data set is needed to compare with the non-partitioning tracer to infer the NAPL saturation (or equivalently volume or mass) for a total of n partitioning tracers data sets. Many suitable activity coefficient models are well known and available for various types of organic liquids and could be used for this purpose. Laboratory experiments may be needed in some cases to test or calibrate these models under the conditions of interest and for representative components of NAPL. Laboratory experiments will still be needed in general to measure the infinite dilution activity coefficients of the tracer components as a function of NAPL composition, but the tracer concentrations will generally be sufficiently low by design that the concentrations of the tracers can be neglected with respect to the activity coefficient model. Very low concentrations of organic components in the NAPL will for similar reasons not be readily inferred by this approach. Thus, if these very small concentrations are known or suspected from other data sources or methods, and if they are considered important even though small, then tracers that are particularly sensitive to these components must be selected and used and repeated applications of the partitioning tracer method may be needed to target specific components or if there is evidence of multiple liquid phases (NAPLs) or significant variations of NAPL composition spatially. Generally, however, these complications will not exist or be important and the use of n-1 partitioning tracers, where n is now the number of major NAPL components, will serve as a sufficient check on the validity of the measured or assumed NAPL composition. This will be particularly advantageous when the method is used as a performance assessment tool since the NAPL composition will in general change as a result of the remediation process itself. For example, co-solvent may selectively extract certain components from certain NAPLs, steam may selectively distill lighter components from certain NAPLS, and similarly for most other remediation processes.

When the tracers are withdrawn, i.e. extracted, from the subsurface formation, the methods and apparatus described above for the introducing step can also be employed. Thus, the tracers can be withdrawn by pumping using an extraction or monitoring well, a piezometer, a stand pipe, a multilevel sampler, a drive point sampler or a cone-penetration sampling point.

The present invention can be practiced in a variety of subsurface formations Thus, a variety of geological units can be present during the practice of the invention. For example, the formation can be uniform and composed of sediment, sediment and rock of varying grain size, rocks with natural fractures and so forth. The present invention can be used to elucidate the presence of NAPL in fractured subsurface formations, as discussed above. The distribution of the nonaqueous phase liquid within the subsurface formation can be irregular. Also, the NAPL can be located in a substantially unconfined formation.

As described above, the NAPLs characterized in accordance with this invention can be LNAPLs (NAPLs less dense than water) or DNAPLs (more dense then water). It is contemplated that the NAPLs constitute contaminants in the subsurface formation. Generally, NAPLs are organic compounds or mixtures of organic compounds. Such contaminants may be needed to be removed from the formation through remediation techniques such as described herein. In a given subsurface formation, mixtures of DNAPLs and LNAPLs may be present. In one embodiment of the invention, DNAPLs are characterized by detecting the presence of the DNAPL, determining the volume of DNAPL, determining the composition of the DNAPL, determining the distribution of the DNAPL or combinations thereof. Representative classes of NAPLs include halogenated hydrocarbons including chlorinated hydrocarbons, hydrocarbons such as alkanes and aromatic compounds, ethers, ketone, aldehydes, petroleum oil distillates such as gasoline and aircraft fuel. Representative examples of DNAPLs include halogenated hydrocarbons such as chlorinated hydrocarbons, creosote and coal tar. Representative chlorinated hydrocarbons include chloromethane, methylene dichloride, chloroform, carbon tetrachloride, ethane substituted with from one to six chlorine atoms, ethene substituted with from one to four chlorine atoms, chlorobenzene, dichlorobenzene and trichlorobenzene. Representative examples of LNAPLs include hydrocarbons including alkanes, aromatic compounds such as benzene, alkyl benzene, biphenyl, alkyl biphenyls, ethers, aldehydes, ketones and crude oil distillates such as gasoline and aircraft fuel.

The present invention can be used to initially detect the presence of NAPL in the subsurface. Additionally, the invention can be carried repeatedly to assess the performance of a remediation by determining the initial volume present of NAPL and then determining the volume present after an attempted remediation. Furthermore, the present invention can be employed to measure the composition of NAPL and/or the volume of NAPL in the subsurface formation.

As used herein, "remediation" means an attempted removal of organic contaminants (NAPL) from a subsurface formation, which can be performed using conventional techniques such as the pump and treat methods, or other techniques well known to those skilled in the art of remediation. Remediation may also be be performed by use of a surfactant solution which is pumped in and extracted from the subsurface to remove the organic contaminants. As used herein, "NAPL saturation" means the volume fraction of NAPL per unit pore space in the subsurface formation. Pore space can be determined by techniques well known to those skilled in the art.

The following examples are provided as exemplary of the practice of the present invention and are not to be construed to limit the scope of the invention or claims thereto. As used in the context of the examples, the injection points may be referred to as "injection wells" and sampling points may be referred to as "production wells".

EXAMPLE 1

Use of Tracers to Determine Presence and Volume of DNAPL in Water-Saturated Sand A soil column experiment was performed to illustrate the use of partitioning tracers to detect DNAPL in a saturated zone. A Kontes preparative chromatography column made of borosilicate glass (4.8 cm ID) was packed with mesh sizes of 60 to 200 Ottawa sand and saturated with water at 23° C. The length of this sandpack was 12.24 cm. The porosity and intrinsic permeability to water were measured and found to be 0.329 and 5.84 Darcy, respectively. Residual tetrachloroethylene (PCE) saturation was established by injecting PCE at a flow rate of 3.31 ml/min for 3.1 pore volumes followed by injecting water at a flow rate of 3.0 ml/min for 3.64 pore volumes at which point the effluent contained only water. Two alcohol tracers were added to the water and 0.52 pore volumes of water containing these tracers were injected at 0.316 ml/min followed by several more pore volumes of water until the Alcohols could no longer be detected in the effluent. The alcohols were isopropanol (IPA), which partitions to the PCE in only very small amounts, and 2,3 dimethyl 2-butanol (DMB), which partitions strongly to the PCE from water. The injected concentration (CO) of IPA was 867 mg/l and the injected concentration of DMB (CO) was 873 mg/l. The partition coefficients of each of these alcohols were determined by equilibrating samples containing in the range of 100 to 1,000 mg/l of both alcohols with equal volumes of water and PCE and measuring the alcohol concentrations in each phase using a gas chromatograph. The partition coefficient for IPA determined by this method was found to be 0.04 and the value for DMB was 2.76. Both of these values are expressed in mg/l of alcohol in the PCE-rich phase divided by mg/l of alcohol in the water-rich phase.

The experimental effluent alcohol concentrations are shown in FIG. 1. As expected, the DMB was retarded relative to the IPA due to its partitioning into the residual PCE. The separation of the two curves gives an unmistakable signal that the sand is contaminated with PCE. The residual PCE saturation was estimated using the method of moments to be 0.189. This value agrees with the value measured from a mass balance on the PCE within the experimental error of each of the measurements. The tracer curves were then numerically simulated using this value and the measured partition coefficients and these are the curves shown in FIG. 1. Only the dispersivity was adjusted in these simulations. The value determined this way was 0.33 cm, which is typical of values measured under these conditions. Inverse modeling was also used to estimate the value of the residual PCE using nonlinear least-squares regression. Each iteration of the computational procedure implementing the nonlinear least-squares regression requires simulating the tracer data twice to evaluate the gradients. The value of the residual PCE saturation computed this way was 0.209.

This experimental example demonstrates that through the practice of this invention, NAPL can be detected in a saturated zone. Similar principles apply to detecting NAPLs in either a saturated or unsaturated zone. There are of course many important details to consider to successfully apply this technology to the detection of NAPLs in the subsurface environment. The analysis of the tracer data becomes much more complicated and subject to large errors if the tracer velocity is to too high for local equilibrium. The velocity in this experiment was 2.51 ft/day, which gave a residence time of the tracers on the order of 4 hours. It is contemplated that this is sufficient residence time to give a close approximation to local equilibrium under these conditions.

Ideally, adsorption of each tracer on the mineral surfaces of the soil should be zero or close to zero for simplicity. However, if the tracer adsorption is measured and it is not too large relative to the retardation due to partitioning into the NAPL, then the calculations can be done accurately even with tracer adsorption. Equal pore volumes of adsorption of the tracers will cancel since only the difference between the response curves affects the estimated residual oil saturation. In any case, adsorption of these alcohol tracers on typical aquifer sand is likely to be negligible compared to the very large partitioning and subsequent differential retardation due to the residual oil saturation of this experiment.

It is expected that there are a number of other tracer performance criteria that may be required for field applications. Some of these are environmental acceptability, chemical and biological stability, acceptable cost and availability in sufficient quantities, ease of detection in the produced fluids, and insensitivity to the precise composition of all components of the NAPL, since this may not be known with high percision. The tracers used in these examples may or may not meet all of these criteria and may or may not be ideal choices for this or any other ground-water condition.

Although less well established, a number of tracers that partition between gas and organic phases have been identified and used. Examples are light alkanes such as ethane. In a contaminated vadose zone, hydrocarbons that are not present could conceivably be used for this purpose, but other tracers such as perfluorocarbons are more likely to be good choices because of their well known and highly desirable properties and the fact that they will not be present even in very low quantities in the contaminated zone. Sulfur hexafluoride is still another potential tracer for injected air. Although it does partition into the organic phase, its partition coefficient may not be large enough for a strong signal under many conditions of interest. Clearly, there are many other possible water and gas tracers for this purpose and there are several advantages to using several tracers rather than the minimum of two tracers.

Figure 2:
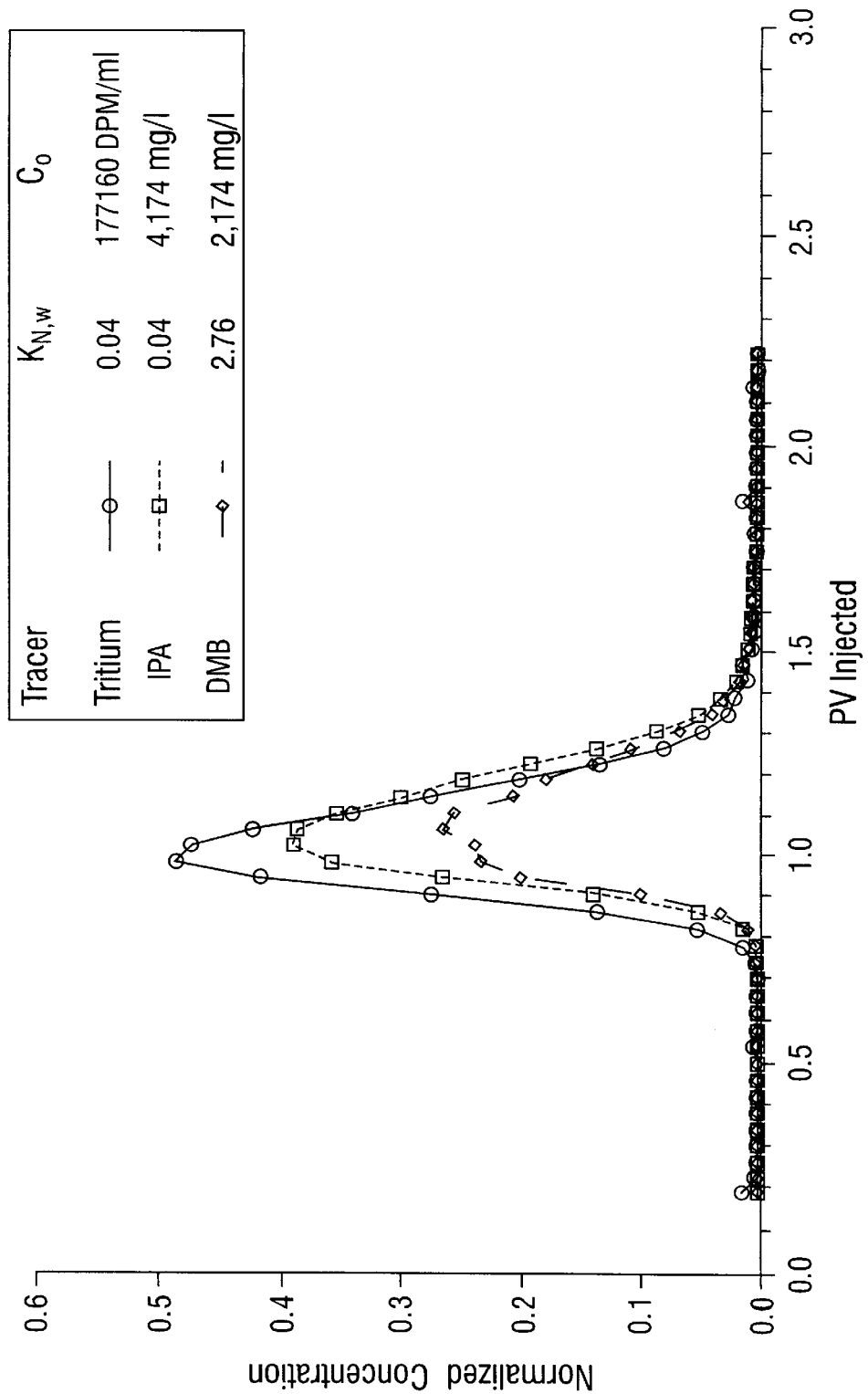
FIG. 2 shows a chromatogram from Example 2 of the results of a partitioning tracer experiment following remediation.

For PCE, IPA has a partitioning coefficient, K, of 0.04 and DMB has a partitioning coefficient, K, of 2.76. The presence of a NAPL, in this case PCE, in the sand is inferred by separation of tracers. In FIG. 2 it should be noted that tritiated water does not partition as does not the IPA to any appreciable degree.

EXAMPLE 2

Performance Assessment of a Remediation

The contaminated sand from Example 1 was cleaned by flushing the sand with an aqueous solution of surfactant until all the trichloroethene was removed to thereby simulate a successful remediation. The procedure of Example 1 was then repeated. The results are shown in FIG. 2. Since no NAPL is present in which DMB can partition into, the IPA and DMB travel through the sand at the same rate and, accordingly, FIG. 2 shows overlap of breakthrough curves of the IPA and DMB. Thus, the absence of NAPL in the sand can be inferred, thereby indicating a successful remediation.

EXAMPLE 3

Use of Tracers to Determine Presence and Volume of DNAPL in Unsaturated Sand

The perfluorocarbon tracers (PFTS) used in this Example were purchased from PCR, Inc. Table 1 lists some of the properties of the selected PFTs as well as those of the other two gases of interest.

The NAPL used to examine the partitioning of perfluorocarbon gases was trichloroethylene (TCE, Certified ACS) obtained from Fisher Scientific. The density of TCE at 20° C. is 1.462 g/cc. Its molecular weight is 131.39 g/mole and its vapor pressure is 1.16 psi at 20° C.

Ottawa sand, purchased from U.S. Silicon, was used in this experiment. The sand has a size range from 40 to 140 U.S. sieve numbers or 0.425 to 0.105 mm. The sand was washed with hydrochloric acid (4N) and baked for 24 hours to remove fine materials and possible organics.

Column Procedures

Three columns were prepared for each experiment: (1) a contaminated primary column (2.5 cm×30 cm) saturated with residual water and TCE; (2) a contaminated pre-column (2.5 cm×60 cm) saturated with water and TCE; and (3) an uncontaminated secondary column (2.5 cm×30 cm) saturated only with water. The contaminated primary column was assembled and weighed without sand in order to obtain a reference weight of the column. This weight was used later to estimate porosity. Next, the inlet end pieces were removed and the column was secured to a vibrating jig. Ottawa sand was placed in a funnel and the funnel was also affixed to the jig. The apparatus was activated and the column was allowed to fill at a rate of approximately 1 cm (of height in column) per minute.

After the primary column was full, it was removed from the stand and the inlet cap tightened onto the end of the column. In addition to the end pieces, three screens (60–150–60 mesh or 0.25–0.0998–0.25 mm) were placed on each end in a sandwich fashion. These assist in distributing the fluid flow and act to keep pressure on the sand pack. Subsequently, the column was leak-tested at a pressure of 10 psi. Finally, the column was weighed again and the porosity and pore volume were estimated to be 35% and 56.9 cc, respectively. The mean grain density of the sand was 2.65 gm/cc.

The contaminated pre-column (2.5 cm×60 cm) was prepared similar to the first column. This column saturates incoming air to reduce stripping of water and TCE from the primary column that was used to evaluate the tracers.

The primary column was mounted in a vertical configuration and a burette with 100 cc of deionized water was mounted above the column and attached to the inlet. The valve on the burette was opened and water was allowed to gravity drain into the column. After approximately one pore volume of water had entered the column, the burette was disconnected and the column was allowed to continue to gravity drain. Air was flushed through the column to displace any mobile water. The difference between the water injected and the water produced was used to determine the residual water saturation. The column was weighed again to verify the water retained. The residual water saturation was estimated to be 35.9%.

Next, approximately 5 cc of TCE, enough to produce a residual saturation, was injected into the primary column using a syringe and allowed to gravity drain. After draining overnight, the column was weighed for a more accurate estimate of TCE saturation. The residual TCE saturation was estimated to be 8.4%. In both cases, water and TCE injection, the pre-column was treated in the same manner. However, larger amounts of water anc. TCE were injected since the pre-column is twice as large.

The primary Column and pre-column were plumbed into the flowpath. Air flow was through the precolumn, past the reference side of the thermal conductivity detector (TCD), to the test column and then to the measurement side of the TCD. Two injectors, one for the gas tracers (Valco Instruments' switching valve with sample loop) and one for liquid tracers (heated injection port) were located between the reference side of the TCD and the test column. Flow rates were adjusted by the use of a snubber valve located between the precolumn and TED. Flow rates were monitored and measured by a combination of rotameters and a bubble meter. The TCD measures the difference between the reference stream and the effluent of the test column. Additionally, water-filled manometers were affixed to each end of the column to measure pressure drops across the column. These measurements were used to estimate the permeability of the sand-pack.

Approximately 4 to 8 hours was required for the air stream to equilibrate and for a stable baseline to be established. When, the baseline was stable, tracer injections began. Data collected from the TCD were integrated and the integration values stored to computer files data acquisition software.

A secondary, uncontaminated column was packed and configured in the same manner as the contaminated column. The only modification made to this column was that the volume of water was equal to the volume of water plus TCE in the primary column. This secondary column was used to observe tracer behavior in an uncontaminated environment.

Using the setup described above, several experiments were conducted at various flow rates to determine flow rate dependency. Additionally, another test column was prepared containing soil from a field site and the tracers were evaluated in this medium.

Results and Discussion

Figure 3:
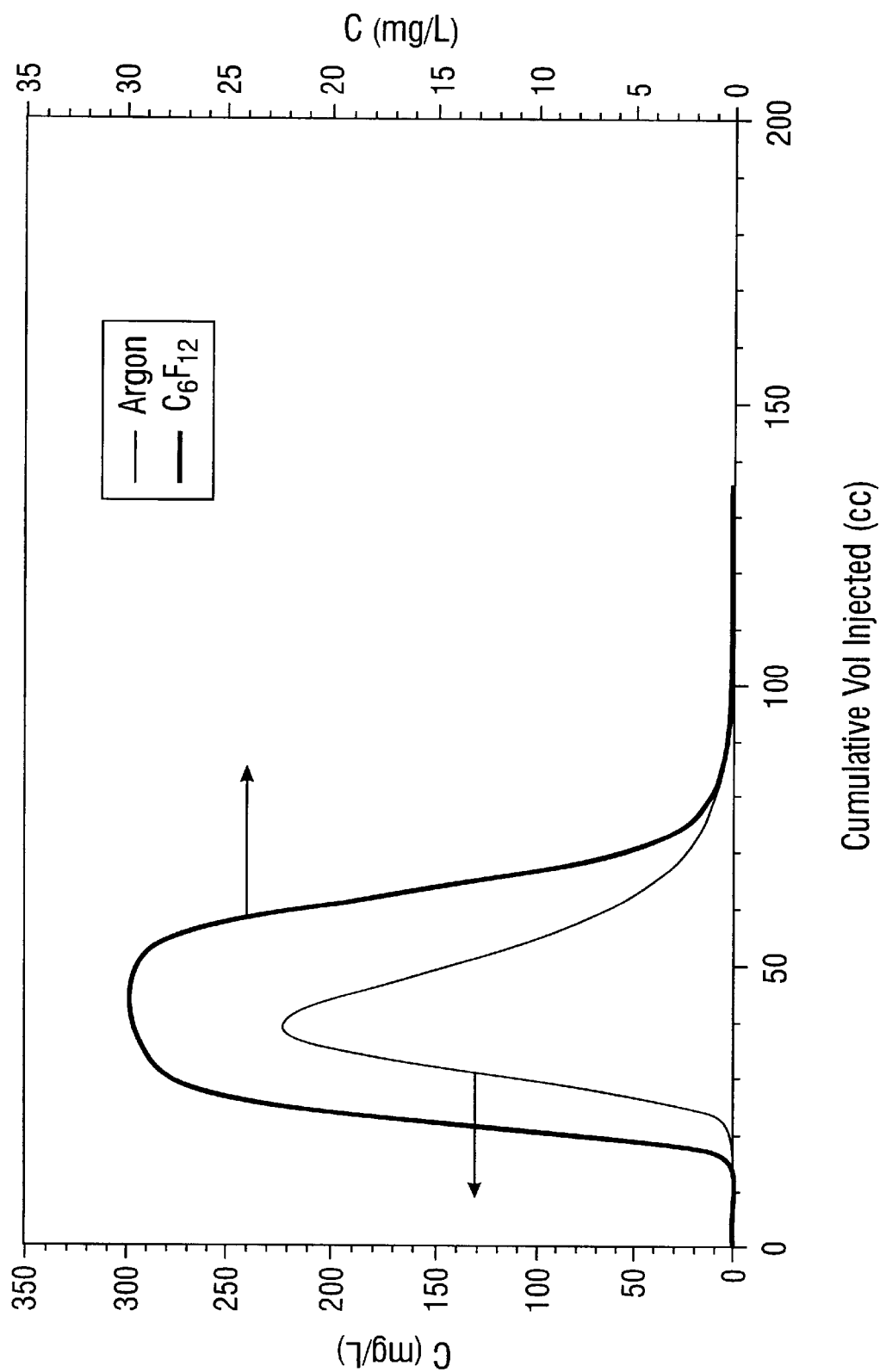
FIG. 3 shows breakthrough curves from Example 3 after injection of tracers through a clean column.

Before tracer injection began in the primary column, argon and $C_6F_{12}$ were injected into the secondary column. Their breakthrough curves are plotted in FIG. 3. Using this procedure, the gas saturation in the secondary column would be similar to that in the primary column. The secondary column was first allowed to equilibrate. Once a baseline was established, argon and $C_6F_{12}$ were injected into the column. The $C_6F_{12}$ was injected as a liquid through the heated injection port. The injector temperature was 40° C.; the liquid was vaporized and moved through the column as a gas. The purpose of this was twofold, first, to monitor the $C_6F_{12}$ with respect to argon; the mean residence times should be similar in a clean column; and second, to observe the breakthrough curve of a liquid tracer (at room temperature and atmospheric pressure) and to examine it for characteristics that may be particular to tracers injected as liquids. Several of the tracers in Table 1 are injected as liquids, in particular $C_5F_8$, $C_6F_{12}$, $C_7F_{14}$, $C_8F_{16}$. When mixed with air, however, they become gases.

The mean residence times were calculated by the method of moments to be 45 cc for both the argon and $C_6F_{12}$ tracers in the secondary column. The mean residence times should be equal since there is no TCE for the tracer to partition into. From this result, it can be inferred that under these conditions adsorption is negligible. Additionally, the $C_6F_{12}$, although injected as a liquid, does not exhibit any substantially different characteristics than argon. The flatness of the peak is believed to be a result of the fact that the liquid vaporizes slowly.

After the uncontaminated column experiment had been completed, the contaminated column experiments were begun. Once a steady baseline on the chart recorder was achieved with the contaminated column connected, the tracers were injected sequentially into the column and their production was monitored. The mean residence time for production of each tracer wag calculated from the response curves using the method of moments. This value can be expressed in minutes or converted to volume units by multiplying by the flow rate. Once the mean residence times were known, the experimental partition coefficient for each tracer was calculated. The ratio of the ideal partition coefficient to that of the experimental value gives the activity coefficient of each tracer in TCE. Table 2 and FIGS. 4, 5 and 6 provide tabular and graphical analysis of the results.

Table 2 lists the mean residence time (in minutes and cc), experimental partition coefficients, and the activity coefficients calculated for each tracer. Argon has the shortest retention time followed by $CF_4$ and $SF_6$. The small retention time for $CF_4$ indicates that its partitioning is essentially zero since the value falls within the range of measurement error compared to argon. However $SF_6$ does show a small but experimentally significant partitioning into the TCE. The table shows that partitioning generally increases with an increase in molecular weight of the tracer.

The computed activity coefficients indicate that high nonideality exists between the perfluorocarbon tracers and TCE. The smallest activity coefficient is 20.3 for $C_5F_8$, which is still substantial. The highest was 63.1 for $C_8F_{16}$.

Figure 4:
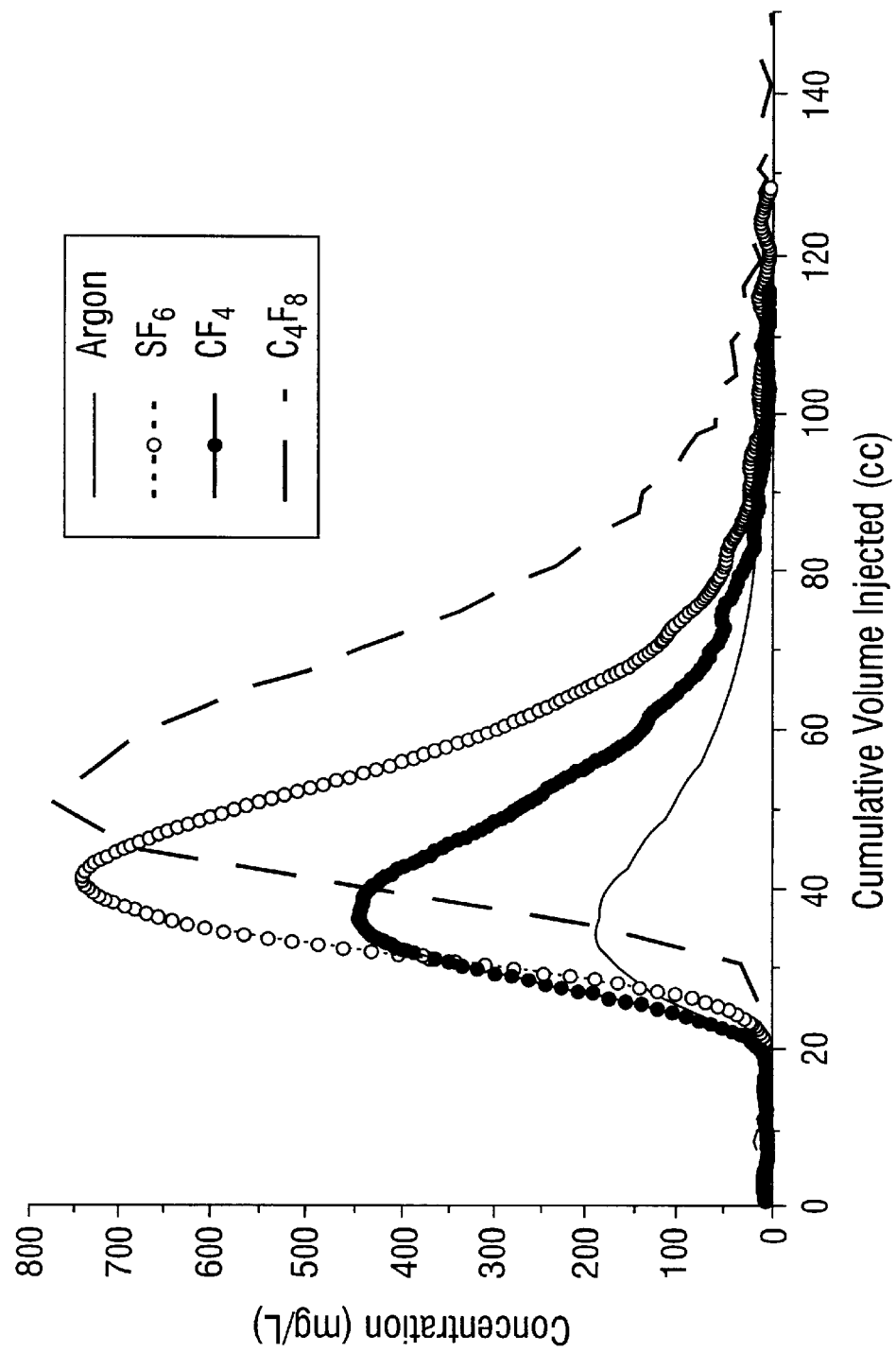
FIG. 4 shows response curves for light tracers used in Example 3.
Figure 5:
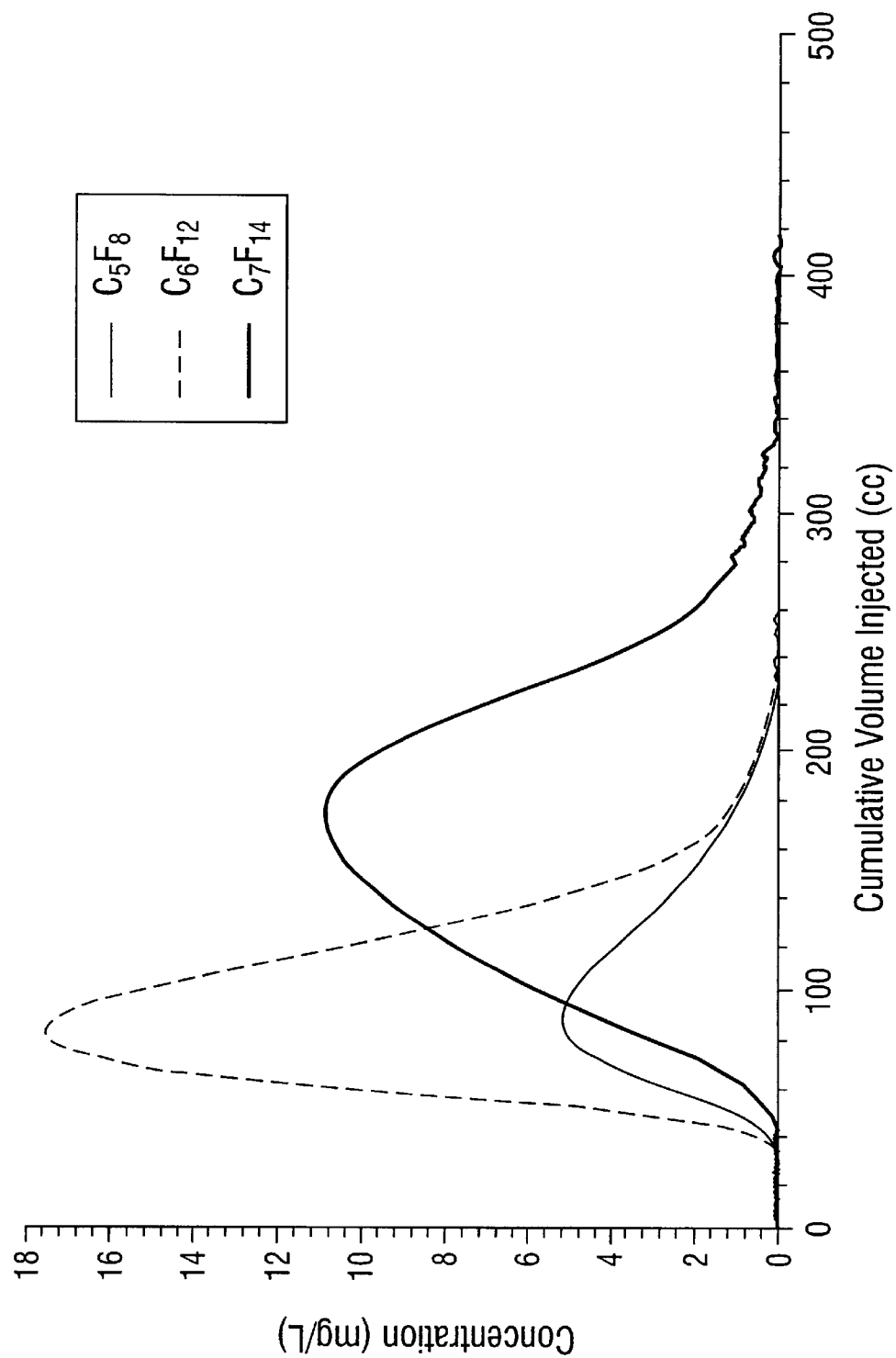
FIG. 5 shows response curves for perfluorocarbon tracers used in Example 3.
Figure 6:
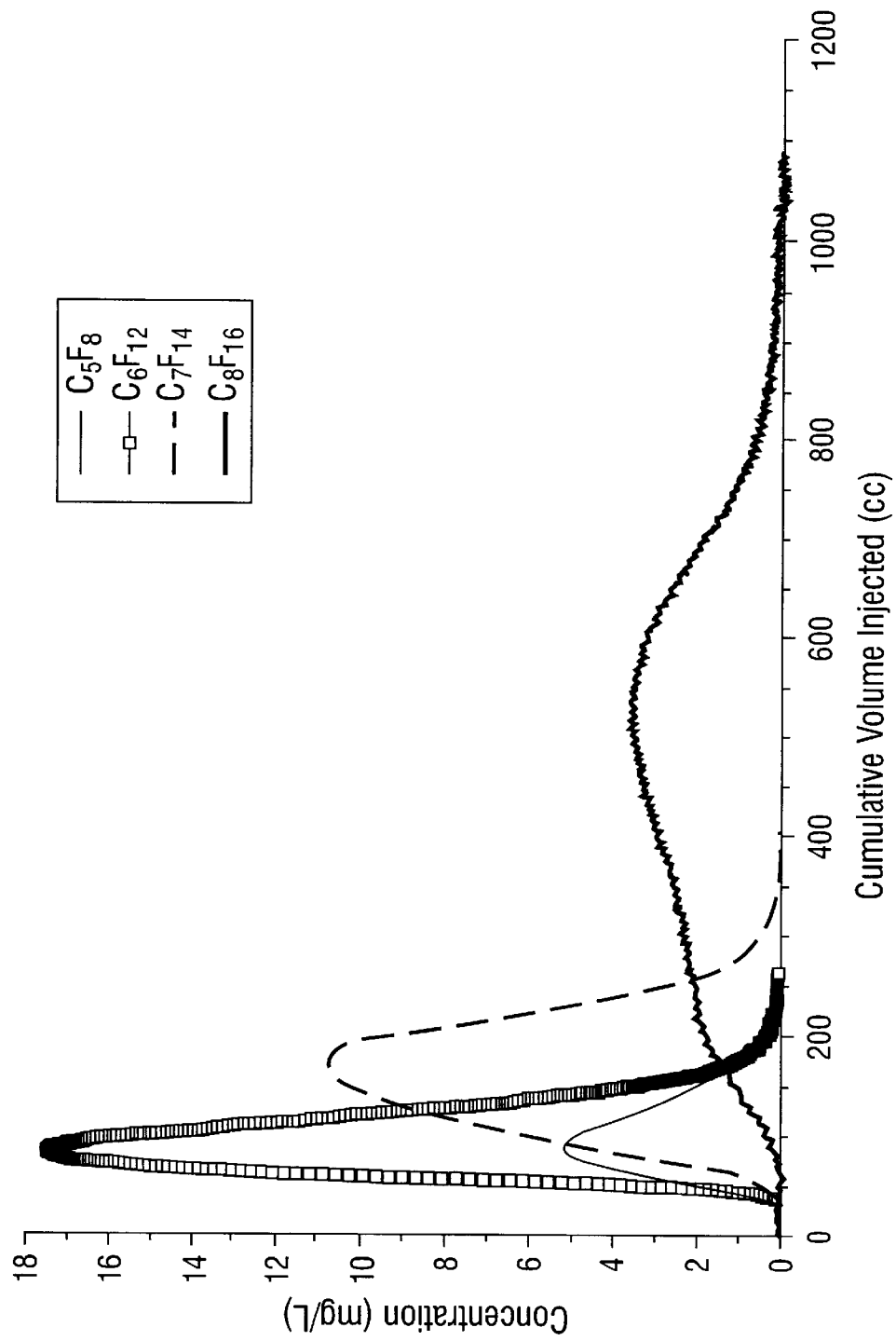
FIG. 6 shows response curves for tracers used in Example 3.

The breakthrough curves are divided into FIGS. 4, 5 and 6. FIG. 4 plots the lighter (gas) tracers (argon, $SF_6$, $CF_4$ and $C_4F_8$) which were observed at much higher concentrations than the heavier tracers ($C_5F_8$, $C_6F_{12}$, $C_7F_{14}$, $C_8F_{16}$). A volume of 3.5 cc of each gas tracer was injected into the column.

FIGS. 5 and 6 show the heavier (liquid) tracers. These tracers are liquids at room temperature and atmospheric pressure. A volume of 0.1 cc of each liquid tracer was injected except 0.05 cc of $C_5F_8$ was injected. The produced tracer concentrations of the heavier tracers could be increased by injecting additional amounts. FIG. 5 does not include $C_8F_{16}$, because of its delayed production from the column. However, it is included in FIG. 6. Clearly the heavier tracers exhibit larger mean residence times relative to argon, the nonpartitioning tracer. In addition, the curve for $C_8F_{16}$ shows some asymmetry early in the curve due to impurities in the tracer.

The tracer response curves generally trend to the right indicating increased partitioning. As the tracer partitions into the NAPL phase, it is retained in the column longer therefore its peak is retarded. The graphical trend is illustrated by the partition coefficient calculations reported in Table 2.

The most prominent trend evident in these results is that as the tracers increase in molecular weight, along with a decrease in vapor pressure, the peak height decreases and there is more spreading at the base of the curve due to increased partitioning. Compared to the uncontaminated column, where the argon and $C_6F_{12}$ had similar mean residence times, with the addition of TCE to the column, these two tracers now differ in the primary column by a factor of more than two.

Further experiments at different flow rates provided additional data about the tracers. Flow rates of 1.38 cc/min and 4.15 cc/min were established and the suite of tracers were injected sequentially into the column at these flow rates. These rates correspond to linear velocities of $2 \times 10^{-4}$ m/s and $6.4 \times 10^{-4}$ m/s. The tracers and their respective partition coefficients are listed in Table 3. The negative partition coefficient of $CF_4$ at 4.15 cc/min implies that $CF_4$ was produced before argon for that experiment. Considering all of the data, the conclusion is that $CF_4$ shows negligible partitioning and should be a good choice for a nonpartitioning tracer.

Figure 7:
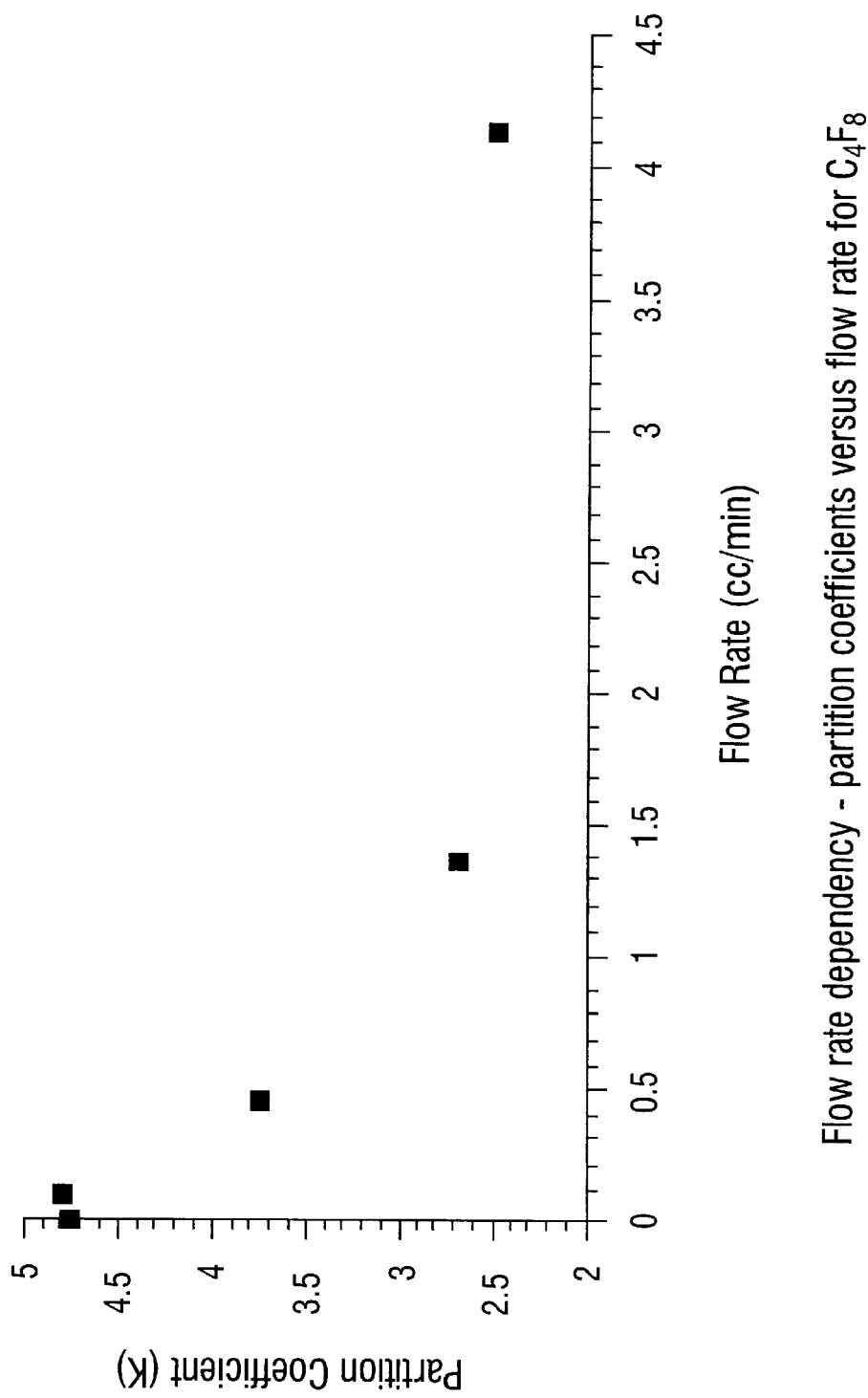
FIG. 7 shows flow rate dependency (partition coefficients) versus flow rate as described in Example 3.

These data indicate that equilibrium partitioning was not occurring at the higher flow rates. Since a rate dependence was observed, the rate was lowered to 0.08 cc/min and the experiment repeated for $C_4F_8$ In addition, a batch equilibrium measurement of the partition coefficient was made for this tracer. Both of these measurements gave a partition coefficient of about 4.7, which is significantly higher than the value of 3.7 at the next lowest rate of 0.45 cc/min. FIG. 7 shows these data for a batch, experiment and all flow rates examined. Based on this data it is contemplated the batch and variable flow rate must be very low in this column experiment for equilibrium partitioning to occur. The regidence time at 0.45 cc/min is about two hours and several times this may be required for equilibrium partitioning. As the partition coefficient increases, so does the residence time, so the heavier tracers should be lean effected by nonequilibrium partitioning. In any case, once suitable tracers have been identified, as has been done here, either batch experiments or experiments at low rates or in longer columns (to give long residence times) can be conducted to determine the equilibrium partitioning coefficients needed for field application (assuming the residence time for the field test is long compared to the column test).

Another experiment was conducted involving the injection of tracers into a column packed with uncontaminated field soil. The porosity of the field soil was 42.6%. The permeability wag estimated to be about 1.3 Darcies; about six times lower than the Ottawa sand. In addition, the field soil contained clays. The soil was contaminated with TCE in the same manner as the previous experiments. The tracers were then injected at two different rates. The lighter tracers ($CF_4$, $C_4F_8$, $C_6F_{12}$ and $SF_6$) were injected at 0.4 cc/min, and the heavier ones ($C_5F_8$, $C_7F_{14}$ and $C_8F_{16}$) at 1.2 cc/min. These rates correspond to linear velocities of $5.8 \times 10^{-5}$ m/s and $1.7 \times 10^{-4}$ m/s, respectively. Argon was injected at both rates. The partition coefficients for the various tracers in field soil are given in Table 4. The $CF_4$ again shows negligible partitioning into the TCE. The other tracers show partitioning similar to the previous experiments. The partition coefficient of $C_4F_8$ is 4.77, almost the same as the batch equilibrium measurement. This indicates a closer approach to equilibrium in this experiment even at the rate of 0.4 cc/min.

TABLE 1

Properties of Gas Tracers Used in Partitioning Tracer Test Experiments

| Tracer | Molecular Weight (gm/mole) | Vapor Press (psi @° C.) | Boiling Pt. (° C.) |
| --- | --- | --- | --- |
| Argon, Ar | 39.95 | — | −186.0 |
| Sulfur Hexafluoride, $SF_6$ | 146.06 | 334 @ 21 | −63.8 |
| Carbon Tetrafluoride; $CF_4$ | 88.01 | — | −128.0 |
| Octafluorocyclobutane, $C_4F_8$ | 200.04 | 40 @ 21 | −5.8 |
| Octafluorocyclopentene, $C_5F_8$ | 212.05 | 12.7 @ 25 | 27.0 |
| Dodecafluorodimethylcyclobutane, $C_6F_{12}$ | 300.06 | 7.2 @ 25 | 45.0 |
| Perfluoromethyleyclohexane, $C_7F_{14}$ | 350.07 | 2.1 @ 25 | 76.0 |
| Perfluoro-1,3-dimethylcyclohexane, $C_8F_{16}$ | 400.07 | 0.67 @ 25 | 101.5 |

TABLE 2

Partition coefficients and activity coefficients from partitioning tracer experiment at 0.45 cc/min with Ottawa sand TCE

| Tracer i | Mean Residence Times $\bar{t}_i$ (mins) | $\bar{t}_i$ (cc) | Ideal $K_i$ ($C_{TCE}/C_{AIR}$) | Exp. $K_i$ ($C_{TCE}/C_{AIR}$) | Activity Coefficient, $\gamma_i$ |
| --- | --- | --- | --- | --- | --- |
| Argon | 93.2 | 41.9 | 0.00 | 0.00 | — |
| $SF_6$ | 103.7 | 46.7 | 11.87 | 1.02 | 11.6 |
| $CF_4$ | 95.1 | 42.8 | — | 0.22 | — |
| $C_4F_8$ | 131.4 | 59.1 | 99.14 | 3.73 | 26.6 |
| $C_5F_8$ | 235.0 | 105.8 | 312.54 | 15.4 | 20.3 |
| $C_6F_{12}$ | 204.4 | 92.0 | 550.81 | 10.6 | 52.0 |
| $C_7F_{14}$ | 362.6 | 163.2 | 1934.45 | 33.2 | 58.3 |
| $C_8F_{16}$ | 1055.0 | 474.8 | 5857.20 | 92.8 | 63.1 |

TABLE 3

Experimental Partition Coefficients ($K_i$) at Various
Flow Rates for Ottawa Sand Contaminated with TCE.

| Tracer | $K_i$ ($C_{TCR}/C_{AIR}$) at 1.38 cc/min | $K_i$ ($C_{TCE}/C_{AIR}$) at 4.15 cc/min |
|---|---|---|
| $SF_6$ | 0.04 | 0.37 |
| $CF_4$ | — | −0.21 |
| $C_4F_8$ | 2.68 | 2.49 |
| $C_5F_8$ | 13.8 | 12.8 |
| $C_6F_{12}$ | 7.53 | 8.70 |
| $C_7F_{14}$ | — | 49 |
| $C_8F_{16}$ | 104.5 | 72.9 |

TABLE 4

Experimental Partition Coefficients ($K_i$) and Activity
Coefficients ($\gamma_i$) in Field Soil Contaminated with TCE.

| Tracer | $K_i$ ($C_{TCE}/C_{AIR}$) | Activity Coefficient, $\gamma_i$ |
|---|---|---|
| $SF_6$ | 0.69 | 17.2 |
| $CF_4$ | 0.12 | — |
| $C_4F_8$ | 4.77 | 20.8 |
| $C_5F_8$ | 18.2 | 17.2 |
| $C_6F_{12}$ | 12.3 | 45 |
| $C_7F_{14}$ | 36.8 | 52.6 |
| $C_8F_{16}$ | 65.3 | 89.7 |

It should be appreciated that additional materials can be added along with the tracers during the practice of this invention. However, it should also be appreciated that this invention can be practiced in the absence of other substances or in the absence of other procedures during the practice of this invention. Thus, the present invention may be practiced in the absence of surfactants which might deleteriously effect the partitioning of tracers in the NAPL

What is claimed is:

1. A method for determining a composition of nonaqueous phase liquid located in a subsurface formation and consisting of a known number n, where n is two or more, of major organic species, comprising:

(A) introducing one or more non-partitioning tracers and at least n partitioning tracers into one or more injection points located in the subsurface formation;

(B) measuring separation between the one or more non-partitioning tracers and the at least n partitioning tracers from one or more sampling points; and (C) comparing the measured separation with a reference separation of the one or more non-partitioning tracers and the at least n partitioning tracers when contacted with nonaqueous phase liquids of known composition to determine the mole fraction of at least one major organic species of the nonaqueous phase liquid in the subsurface formation.

2. The method of claim 1, wherein two or more injection points are employed at different depths.

3. The method of claim 1, wherein two or more sampling points are employed at different depths.

4. The method of claim 1, wherein the injection point and the sampling point are the same.

5. The method of claim 1, further comprising:
    performing an attempted remediation to treat or remove nonaqueous phase liquid in the subsurface formation;
    repeating steps (A)–(C) to assess performance of the attempted remediation.

6. The method of claim 1, further comprising determining the volume of nonaqueous phase liquid in the subsurface formation.

7. The method of claim 1, wherein the nonaqueous phase liquid is more dense than water.

8. The method of claim 7, wherein the nonaqueous phase liquid is a chlorinated hydrocarbon, creosote or coal tar.

9. The method of claim 1, wherein the distribution of the nonaqueous phase liquid is irregular.

10. The method of claim 1, wherein the nonaqueous phase liquid is located in a substantially unconfined formation.

11. The method of claim 1, wherein one or more of the partitioning tracers are reactive tracers.

12. The method of claim 11, wherein at least one of the reactive tracers is chemically reactive.

13. The method of claim 11, wherein at least one of the reactive tracers is biologically reactive.

14. The method of claim 11, wherein a thickening agent is introduced with the tracers.

15. The method of claim 1, further comprising determining the composition of the nonaqueous phase liquid by:
    expressing each tracer partitioning coefficient as a function of activity coefficients for two or more of said components; and
    calculating the respective mole fractions for each of said two or more components and volume of total nonaqueous phase liquid by simultaneously solving the following equation expressed in term of each of said components and said volume of total nonaqueous phase liquid:

$$V_N = (\overline{V}_p - \overline{V}_n)/K$$

where: $\overline{V}_p$ = the first moment of one of said partitioning tracers in terms of cumulative volume of detected tracer at the sampling point;
    $\overline{V}_n$ = the first moment of one of said nonpartitioning tracers in terms of cumulative volume of detected tracer at the sampling point;
    K is the partition coefficient of one of said partitioning tracers; and
    $V_N$ is the volume of total NAPL.

16. The method of claim 6, wherein a volume of total nonaqueous phase liquid in said subsurface formation is determined using the following equation:

$$V_N = (\overline{V}_p - \overline{V}_n)/K$$

where: $\overline{V}_p$ = the first moment of one of said partitioning tracers in terms of cumulative volume of detected tracer at the sampling point;
    $\overline{V}_n$ = the first moment of one of said nonpartitioning tracers in terms of cumulative volume of detected tracer at the sampling point;
    K is the partition coefficient of one of said partitioning tracers; and
    $V_N$ is the volume of total NAPL.

17. The method of claim 16, wherein samples are taken at two or more sampling points located in the subsurface formation, the two or more sampling points being at different depths.

18. The method of claim 1, wherein one or more of the partitioning tracers is a substance which hydrolyzes to form an alcohol and a carboxylic acid.

19. The method of claim 1, wherein one or more of the partitioning tracers is capable of being used as a fuel or nutrient for microorganisms.

20. The method of claimed 1, wherein the presence or absence of nonaqueous phase liquid in said subsurface formation is unknown.

21. The method of claim 20, wherein the tracers are introduced at two or more injection points located in the subsurface formation, the two or more injection points being at different depths.

22. The method of claim 20, wherein samples are taken at two or more sampling points located in the subsurface formation, the two or more sampling points being at different depths.

23. The method of claim 20, wherein the injection point and the sampling point are the same.

24. The method of claim 20, further comprising:
performing an attempted remediation to treat or remove nonaqueous phase liquid in the subsurface formation;
repeating steps (A)–(C) to assess performance of the attempted remediation.

25. The method of claim 20, further comprising determining the volume of nonaqueous phase liquid in the subsurface formation.

26. The method of claim 20, wherein the nonaqueous phase liquid comprises dense nonaqueous phase liquid.

27. The method of claim 20, wherein the nonaqueous phase liquid is a chlorinated hydrocarbon, creosote or coal tar.

28. The method of claim 20, wherein the distribution of the nonaqueous phase liquid is irregular.

29. The method of claim 20, wherein the nonaqueous phase liquid is located in a substantially unconfined formation.

30. The method of claim 20, wherein one or more of the one or more partitioning tracers are reactive tracers.

31. The method of claim 30, wherein at least one of the reactive tracers is chemically reactive.

32. The method of claim 30, wherein at least one of the reactive tracers is biologically reactive.

33. The method of claim 20, wherein a thickening agent is introduced with the tracers.

34. The method of claim 20, wherein said nonaqueous phase liquid comprises two or more components, and further comprising determining the composition of the nonaqueous phase liquid by:
expressing each tracer partitioning coefficient as a function of activity coefficients for two or more of said components; and
calculating the respective mole fractions for each of said two or more components and volume of total nonaqueous phase liquid by simultaneously solving the following equation expressed in terms of each of said components and said volume of total nonaqueous phase liquid:

$$V_N = (\overline{V}_p - \overline{V}_n)/K$$

where: $\overline{V}_p$ = the first moment of one of said partitioning tracers in terms of cumulative volume of detected tracer at the sampling point;
$\overline{V}_n$ = the first moment of one of said nonpartitioning tracers in terms of cumulative volume of detected tracer at the sampling point;
K is the partition coefficient of one of said partitioning tracers; and
$V_N$ is the volume of total NAPL.

35. The method of claim 25, wherein a volume of total nonaqueous phase liquid in said subsurface formation is determined using the following equation:

$$V_N = (\overline{V}_p - \overline{V}_n)/K$$

where: $\overline{V}_p$ = the first moment of one of said partitioning tracers in terms of cumulative volume of detected tracer at the sampling point;
$\overline{V}_n$ = the first moment of one of said nonpartitioning tracers in terms of cumulative volume of detected tracer at the sampling point;
K is the partition coefficient of one of said partitioning tracers; and
$V_N$ is the volume of total NAPL.

36. The method of claim 35, wherein samples are taken at two or more sampling points located in the subsurface formation, the two or more sampling points being at different depths.

37. The method of claim 20, wherein one or more of the partitioning tracers is a substance which hydrolyzes to form an alcohol and a carboxylic acid.

38. The method of claim 20, wherein one or more of the partitioning tracers is capable of being used as a fuel or nutrient for microorganisms.

39. The method of claim 7, wherein the tracers are introduced at two or more injection points located in the subsurface formation, the two or more injection points being at different depths.

40. The method of claim 7, wherein samples are taken at two or more sampling points located in the subsurface formation, the two or more sampling points being at different depths.

41. The method of claim 7, wherein the injection point and the sampling point are the same.

42. The method of claim 7, further comprising:
performing an attempted remediation to treat or remove nonaqueous phase liquid in the subsurface formation;
repeating steps (A)–(C) to assess performance of the attempted remediation.

43. The method of claim 7, further comprising determining the volume of dense nonaqueous phase liquid in the subsurface formation.

44. The method of claim 7, wherein the distribution of the nonaqueous phase liquid is irregular.

45. The method of claim 7, wherein the nonaqueous phase liquid is located in a substantially unconfined formation.

46. The method of claim 7, wherein one or more of the one or more partitioning tracers are reactive tracers.

47. The method of claim 46, wherein at least one of the reactive tracers is chemically reactive.

48. The method of claim 46, wherein at least one of the reactive tracers is biologically reactive.

49. The method of claim 7, wherein a thickening agent is introduced with the tracers.

50. The method of claim 7, wherein said dense nonaqueous phase liquid comprises two or more components, and further comprising determining the composition of the nonaqueous phase liquid by:
expressing each tracer partitioning coefficient as a function of activity coefficients for two or more of said components; and
calculating the respective mole fractions for each of said two or more components and volume of total nonaqueous phase liquid by simultaneously solving the following equation expressed in terms of each of said components and said volume of total nonaqueous phase liquid:

$$V_N = (\overline{V}_p - \overline{V}_n)/K$$

where: $\overline{V}_p$ = the first moment of one of said partitioning tracers in terms of cumulative volume of detected tracer at the sampling point;

$\overline{V}_n$=the first moment of one of said nonpartitioning tracers in terms of cumulative volume of detected tracer at the sampling point;

K is the partition coefficient of one of said partitioning tracers; and $V_N$ is the volume of total NAPL.

51. The method of claim 43, wherein a volume of total dense nonaqueous phase liquid in said subsurface formation is determined using the following equation:

$$V_N = (\overline{V}_p - \overline{V}_n)/K$$

where: $\overline{V}_p$=the first moment of one of said partitioning tracers in terms of cumulative volume of detected tracer at the sampling point;

$\overline{V}_n$=the first moment of one of said nonpartitioning tracers in terms of cumulative volume of detected tracer at the sampling point;

K is the partition coefficient of one of said partitioning tracers; and

VN is the volume of total NAPL.

52. The method of claim 51, wherein samples are taken at two or more sampling points located in the subsurface formation, the two or more sampling points being at different depths.

53. The method of claim 7, wherein one or more of the partitioning tracers is a substance which hydrolyzes to form an alcohol and a carboxylic acid.

54. The method of claim 7, wherein one or more of the partitioning tracers is capable of being used as a fuel or nutrient for microorganisms.

55. A method for determining mole fractions of components of a nonaqueous phase liquid located in a subsurface formation, the liquid having two or more components, comprising:

(A) selecting an assumed mole fraction for each of the N, where N is two or more, selected components to represent an assumed composition of the nonaqueous phase liquid;

(B) selecting at least N partitioning tracers for the assumed composition of the nonaqueous liquid and determining a partition coefficient for each partitioning tracer;

(C) introducing one or more non-partitioning tracers and at least N partitioning tracers into one or more injection points located in the subsurface formation;

(D) recovering one or more non-partitioning tracers and at least one of the at least N partitioning tracers from the subsurface formation at one or more recovery points located in the subsurface formation and measuring to develop a plurality of measured concentrations of the non-partitioning and the partitioning tracers;

(E) using the plurality of measured concentrations for the one or more non-partitioning tracers, developing a plurality of calculated concentrations for at least one of the at least N partitioning tracers using the partition coefficient determined in step (B); and (F) adjusting the assumed mole fraction for the N components until the plurality of calculated concentrations match the plurality of measured concentrations of the tracers, thereby determining mole fractions of the N components.

56. The method of claim 55 wherein step (F) is performed using an inverse method for parameter estimation.

57. The method of claim 56 wherein the inverse method uses a least squares regression algorithm.

58. The method of claim 55 wherein the step of determining partition coefficients of the N partitioning tracers includes experimental measurements.

59. The method of claim 55 wherein the step of determining partition coefficients of the N partitioning tracers includes use of activity coefficient models.

60. The method of claim 55 wherein at least one of the partitioning tracers is selected to have a partition coefficient sensitive to one component of the nonaqueous phase liquid.

61. The method of claim 55 wherein at least one of the components of step (A) is a mixture.

62. A method for determining mole fractions of components of a nonaqueous phase liquid located in a subsurface formation, the liquid having two or more components and a total volume, comprising:

(A) selecting an assumed mole fraction for each of the N, where N is two or more, selected components to represent an assumed composition of the nonaqueous phase liquid;

(B) selecting at least N partitioning tracers for the assumed composition of the nonaqueous phase liquid and determining a partition coefficient for each of the at least N partitioning tracers;

(C) introducing one or more non-partitioning tracers and at least N partitioning tracers into one or more injection points located in the subsurface formation;

(D) recovering one or more non-partitioning tracers and at least two of the N partitioning tracers from the subsurface formation at one or more recovery points located in the subsurface formation and measuring to form a plurality of measured concentrations of the non-partitioning and the partitioning tracers;

(E) using the plurality of measured concentrations of the tracers for the one or more non-partitioning tracers, developing a calculated total volume of the nonaqueous phase liquid using method of moments equations and the plurality of measured concentrations of at least two of the N partitioning tracers and the partition coefficient determined in step (B) for each of the N partitioning tracers; and (F) adjusting the assumed mole fraction for the N components until the total volume of the nonaqueous phase liquid calculated from the first moment of at least two of the N partitioning tracers agrees, thereby determining the mole fractions of at least two of the N components.

63. The method of claim 62 wherein step (F) is performed using an inverse method for parameter estimation.

64. The method of claim 63 wherein the inverse method uses a least squares regression algorithm.

65. The method of claim 62 wherein the step of determining partition coefficients of the N partitioning tracers includes experimental measurements.

66. The method of claim 62 wherein the step of determining partition coefficients of the N partitioning tracers includes use of activity coefficient models.

67. The method of claim 62 wherein at least one of the partitioning tracers is selected to have a partition coefficient sensitive to one component of the nonaqueous phase liquid.

68. The method of claim 62 wherein at least one of the components of step (A) is a mixture.

* * * * *